United States Patent [19]
John et al.

[11] Patent Number: 5,852,207
[45] Date of Patent: Dec. 22, 1998

[54] PROCESS FOR PRODUCING CYANOFORMATE ESTERS

[75] Inventors: Thomas V. John, Yardley; Gerald L. Larson, Newton, both of Pa.; Chitoor S. Subramaniam, East Brunswick, N.J.

[73] Assignee: Creanova Inc., Somerset, N.J.

[21] Appl. No.: 898,571

[22] Filed: Jul. 22, 1997

[51] Int. Cl.⁶ .................................................. C07C 229/00
[52] U.S. Cl. ............................................ 560/155; 562/869
[58] Field of Search ............................... 562/869; 560/155

[56] References Cited

U.S. PATENT DOCUMENTS 4,620,022 10/1986 Findeisen .................................. 556/417

OTHER PUBLICATIONS

Lidy, Tetrahedron Letters, No. 17, pp. 1449–1450, 1973.

*Primary Examiner*—Michael L. Shippen
*Attorney, Agent, or Firm*—Abelman, Frayne & Schwab

[57] ABSTRACT

Alkyl, aralkyl or aryl cyanoformate esters having from one to 20 carbon atoms are prepared by anhydrously reacting stoichiometric amounts of the corresponding alkyl, aralkyl or aryl haloformate and an organosilyl nitrile in the presence of a catalytic amount of a tertiary amine base, preferably 1,4-diazabicyclo[2.2.2]octane, in the absence or presence of an inert solvent. The reaction is conducted at a temperature of from about −30° C. to 70° C., preferably at from about 5° C. to 30° C.

22 Claims, No Drawings

PROCESS FOR PRODUCING CYANOFORMATE ESTERS

FIELD OF THE INVENTION

The invention relates to the commercial preparation of cyanoformate esters.

BACKGROUND OF THE INVENTION

The present invention relates to an economically feasible process for producing $C_1$–$C_{20}$ alkyl, aralkyl and aryl cyanoformate esters in commercial quantities of high purity and in very high yields. Alkyl cyanoformates, especially ethyl cyanoformate, are widely used as intermediates in the manufacture of pharmaceuticals, herbicides, bactericides, insecticides and a variety of other products.

Alkyl cyanoformates have been prepared by reaction of the alkyl haloformates with potassium cyanide in the presence of macrocyclic polyethers (also known as crown ethers.) Childs and Weber, in "Preparation of Cyanoformates, Crown Ether Phase Transfer Catalysis", J. Org. Chem. Vol. 41, 346(1976), report obtaining isobutyl cyanoformate in a 94% yield via the reaction of isobutyl chloroformate with potassium cyanide in methylene chloride in the presence of 18-crown-6. However, the large excess and toxicity of methylene chloride used and the relatively high cost of crown ethers renders this process unattractive for large-scale commercial manufacturing.

The preparation of alkyl cyanoformate derivatives by the reaction of an alkyl haloformate in methylene chloride with aqueous sodium cyanide employing a quaternary ammonium phase transfer catalyst and at very low temperatures is described in U.S. Pat. No. 4,539,422 issued in 1985. The extreme conditions and excessive waste involved in this process renders it impractical and unattractive for large-scale commercial production.

It is known from Japanese patent 55(1980) 79,356 to produce cyanoformate esters by the reaction of oxamidic acid esters, phosgene and tertiary amines. A yield of 82% ethyl cyanoformate was reported. In Swiss patent CH 675, 875 (1990) a similar yield of ethyl cyanoformate was reported from the reaction of hydrogen cyanide, ethyl chloroformate and triethylamine in an inert solvent. These processes disadvantageously involve the isolation and removal of a mole-equivalent of tertiary amine hydrochloride salt from the product mixture.

Lidy and Sundermeyer, in Tet. Lett. 1449(1973), reported the formation of ethyl and methyl cyanoformates in approximately 70% yields by the reaction at refluxing temperatures of the appropriate chloroformate with trimethylsilyl nitrile in the presence of pyridine as a catalyst. Replication of this process revealed that it proceeded very slowly at room temperature (25° C.), and that the reaction did not go to completion at reflux, thereby necessitating a separation of the product from the remaining starting materials.

The use of triethylenediamine, or 1,4-diazabicyclo [2.2.2] octane, is disclosed in U.S. Pat. No. 4,620,022 as a catalyst in processes for the production of specified substituted trimethylsilyloxymalonic acid dinitrile compounds in which the starting material includes an acid halide and trimethylsilyl nitrile. Other base and acid catalysts are disclosed as useful in various alternative embodiments of the disclosed process.

SUMMARY OF THE INVENTION

A $C_1$–$C_{20}$ alkyl, aralkyl, or aryl cyanoformate ester is prepared by anhydrously reacting stoichiometric amounts of the corresponding $C_1$–$C_{20}$ alkyl, aralkyl or aryl haloformate and organosilyl nitrile in the presence of a catalytic amount of a tertiary amine base, preferably 1,4-diazabicyclo[2.2.2] octane, in the absence or presence of an inert solvent. The reaction is performed at a temperature of from about −30° C. to 70° C., and preferably at from about 5° C. to 30° C., and most preferably at ambient temperature, i.e., 20° C.–25° C. The reaction proceeds under ambient pressure.

DETAILED DESCRIPTION OF THE INVENTION

Using the process of the invention, $C_1$–$C_{20}$ alkyl, aralkyl or aryl cyanoformates are prepared by reacting approximately one equivalent of the corresponding $C_1$–$C_{20}$ alkyl, aralkyl or aryl haloformate, preferably a chloroformate, with an organosilyl nitrile, preferably an alkylsilyl nitrile and most preferably trimethylsilyl nitrile, in the presence of a catalytic amount of a tertiary amine base, such as triethylamine, 1,4-dizabicyclo[2.2.2]octane ("DABCO"), 1,8-diazabicyclo[5.4.0]undec-7-ene ("DBU"), N,N-dimethylaminopyridine ("DMAP"), or pyridine, and preferably 1,4-diazabicyclo[2.2.2]octane, at a temperature in the range from about −30° C. to 70° C., and preferably at room temperature, i.e., about 20° C. to 25° C. The reaction proceeds according to the following scheme:

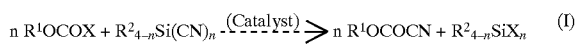

where $R^1$ is a $C_1$–$C_{20}$ alkyl, aralkyl, or aryl; $R^2$ is a lower alkyl, i.e. $C_1$–$C_6$; and X is a halogen, i.e., F, Cl, Br or I, and n is 1–3.

The process of the invention has been found to consistently produce the corresponding $C_1$–$C_{20}$ alkyl, aralkyl, or aryl cyanoformates of high purity and in very high yields.

The use of an inert solvent such as toluene, ether or hexane has no adverse effect on the outcome of the process. However, to limit handling of the toxic product and to maximize yield and purity, it is preferred to practice the process in the absence of a solvent.

The reaction must be performed under substantially anhydrous conditions, since water decomposes the product and the organosilyl nitrile. It is preferred, therefore, that both the vessel and the reagents should be carefully dried before commencing the reaction in order to obtain the best results.

The reaction can be carried out at a temperature in the range of from about −30° C. to 70° C., and preferably at from about 5° C. to 30° C. The reaction can be carried out at a temperature below 5° C. or exceeding 30° C., but there is no apparent advantage in doing so. An inert gas atmosphere can be applied, preferably nitrogen, but is not required.

The haloformate derivatives, in particular the chlorides, are inexpensive and readily available.

The organosilyl nitrile is preferrably an alkylsilyl nitrile, where the alkyl contains from one to six carbon atoms. In a preferred embodiment, the alkylsilyl nitrile is selected from the group comprising trimethylsilyl nitrile, dimethydicyanosilane and methyltricyanosilane. The most preferred organosilyl nitrile is trimethylsilyl nitrile since it can be prepared in situ from inexpensive starting materials, as taught in U.S. Pat. No. 5,258,534. To minimize cost, the by-product trimethylsilyl chloride can be recycled to produce trimethylsilyl nitrile.

As shown in Table I, use of the process of the invention produces $C_1$–$C_{20}$ alkyl, aralkyl or aryl cyanoformates of high purity and in excellent yields. The yields of cyanoformates obtained can exceed 95% of theoretical and the product purity is generally greater than 98% as determined by gas chromatographic analysis. Generally, the reaction proceeds rapidly at ambient temperature (i.e., about 25° C.), and for most constituents can be carried out in a few hours.

The solvent-free conditions used in the process of the invention substantially reduce the handling of the highly toxic products and provide maximum yields of the desired product. No salts are produced in the process and the desired product is recovered by distillation. Furthermore, the by-product from the preferred organosilyl nitrile, trimethylsilyl chloride, can be recycled to produce trimethylsilyl nitrile, thus rendering this a waste-free process for producing cyanoformate derivatives that creates no unwanted by-products requiring treatment or disposal. The process of the invention thereby avoids the problems and expenses associated with the processes of the prior art.

The following examples are illustrative of the wide range of products that can be obtained in the practice of the process of the invention.

EXAMPLE 1

Ethyl Cyanoformate

Fifty five grams (0.51 mol) of ethyl chloroformate and 0.10 g (0.9 mmol) of 1,4-diazabicyclo[2.2.2]octane were added to a dry reaction vessel under a dry nitrogen atmosphere, stirred and cooled to approximately 20° C. using a water bath. Trimethylsilyl nitrile (51 g; 0.51 mol) was then added dropwise over about 1 hr. The mixture was maintained between 20°–30° C. until the reaction reached completion (approximately 2–3 hr.) The trimethylsilyl chloride was removed by distillation under reduced pressure, and 48 g of product was isolated as a colorless liquid (bp 50° C./8 mm Hg.) Yield: 96.3% (theoretical); purity 98.5%(GC assay); $^1$H-NMR: $\delta$4.4, q(2 H), J=7 Hz, $\delta$1.4, t(3H), J=7 Hz; IR: 2250 cm$^{-1}$ (CN), 1750 cm$^{-1}$ (CO).

In the following examples, the indicated cyanoformates were prepared in accordance with the same procedure that was used in Example 1 to produce products having the physical characteristics indicated.

EXAMPLE 2

Isobutyl Cyanoformate

Isobutyl chloroformate (68.3 g; 0.5 mol), trimethylsilyl nitrile (49.5 g; 0.5 mol) and 1,4-diazabicyclo[2.2.2]octane (0.10 g; 0.9 mmol) was reacted to produce 61.5 g of isobutyl cyanoformate as a clear, colorless liquid (bp 52°–53° C./20 mmHg) Yield: 97% (theoretical); 98% purity $^1$H-NMR: $\delta$4.1,d(2H), J=7 Hz; $\delta$2.1, m(1H), $\delta$1.00,d(6 H), J=7 Hz; IR 2250 cm$^{-1}$ (CN), 1750 cm$^{-1}$ (CO).

EXAMPLE 3

Propyl Cyanoformate

Propyl chloroformate (10 g; 0.08 mol), trimethylsilyl nitrile (8 g; 0.08 mol) and 1,4-diazabicyclo[2.2.2]octane (0.01 g; 0.09 mmol) were reacted to give propyl cyanoformate, 8.4 g as a clear, colorless liquid (bp 25°–27° C./10 mm Hg.) Yield 93% (theoretical); purity 98% $^1$H-NMR: $\delta$4.6, t(2H), J=7 Hz, $\delta$1.8, m(2H), $\delta$1.00, t(3 H), J=7 Hz; IR 2250 cm$^{-1}$(CN), 1750 cm$^{-1}$ (CO).

EXAMPLE 4

Methyl Cyanoformate

To a mixture of methyl chloroformate (4.73 g; 0.05 mol) and 1,4-diazabicyclo [2.2.2] octane (5 mg; 0.05 mmol) was added dropwise trimethylsilyl nitrile (5.0 g; 0.05 mol) and the mixture maintained at 20°–25° C. for about 1–2 hr with stirring. The resulting methyl cyanoformate was identified by gas chromatography and spectroscopy. $^1$H-NMR: $\delta$4.0, s(3H); IR: 2250 cm$^{-1}$ (CN), 1750 cm$^{-1}$ (CO).

EXAMPLE 5

Benzyl Cyanoformate

Benzyl chloroformate (13.7 g; 0.08 mol) and 1,4-diazabicyclo [2.2.2] octane (60 mg; 0.54 mmol) were added to a dry reaction vessel under a dry nitrogen atmosphere. Trimethylsilyl nitrile (8 g; 0.08 mol) was added dropwise over about 1 hr. The mixture was maintained at between 20°–30° C. until the reaction reached completion in about 3 hr. After distilling off the trimethylsilyl chloride, 10.6 g product was isolated as a clear liquid (bp 70–72/1 mm Hg.) Yield: 82%; purity 98% $^1$H-NMR: $\delta$7.3,m(5H); $\delta$5.26, s(2H); IR: 2250 cm$^{-1}$ (CN), 1760 cm$^{-1}$ (CO).

EXAMPLE 6

Phenyl Cyanoformate

Phenyl chloroformate (3.16 g; 0.020 mol) and 1,4-diazabicyclo [2.2.2] octane (12 mg; 0.11 mmol) were added to a dry reaction vessel under a dry nitrogen atmosphere, followed by addition of trimethylsilyl nitrile (2.0 g; 0.02 mol). The mixture was maintained at between 20°–30° C. until the reaction reached completion in about 12 hr. After distilling off the trimethylsilyl chloride under reduced pressure, 2.70 g of the product was isolated as a solid (mp 48°–50° C.) Yield: 92%; purity 98% $^1$H-NMR: $\delta$7.3,m (5H); IR: 2250 cm$^{-1}$ (CN), 1760 cm$^{-1}$ CO.

In the following example, an alkyl cyanoformate was prepared using the pot residue from a previous batch which contained catalyst after removal of the product and the trimethylsilyl chloride by-product.

EXAMPLE 7

Ethyl Cyanoformate from Recycled Catalyst

Two grams (0.02 mol) of ethyl chloroformate and 0.10 g of pot residue from a previous run containing 1,4-diazabicyclo[2.2.2]octane were added to a dry reaction vessel under a dry nitrogen atmosphere, stirred and cooled to approximately 20° C. using a water bath. Trimethylsilyl nitrile (2 g; 0.02 mol) was then added dropwise and the mixture maintained at between 20°–30° C. A GLC trace of the reaction mixture showed complete conversion to ethyl cyanoformate indicating that the previously used catalyst was active in driving the reaction to completion.

A summary of the yields and physical characteristics of the products obtained in Examples 1 through 6 above are set forth in Table I for the reaction of chloroformate having the indicated substituent $R^1$ and trimethylsilyl nitrile to produce the indicated cyanoformates by the practice of the invention.

TABLE I

| $R^1$ | Yield (%) | BP, °C. (mm) |
|---|---|---|
| Methyl | 94 | — |
| Ethyl | 96 | 68–70 (100) |
| Propyl | 93 | 25–27 (10) |
| Isobutyl | 97 | 52–53 (20) |
| Benzyl | 82 | 70–72 (1) |
| Phenyl | 92 | 48–50 (mp) |

EXAMPLE 8

Ethylcyanoformate from Dimethyldicyanosilane

To a mixture of ethylchloroformate (5.4g; 0.05 mol) and 1,4-diazabicyclo [2.2.2] octane (0.01 g; 0.01 mmol) is added dropwise, dimethyldicyanosilane (5.5 g; 0.05 mol). The mixture is maintained at between 50° to 30° C. for 2–5 hr. After distilling off the dimethyldichlorosilane, the ethylcyanoformate is isolated by distillation under reduced pressure. The ethylcyanoformate product purity and yield are comparable to those of Example 1.

EXAMPLE 9

Ethylcyanoformate from Methyltricyanosilane

To a mixture of ethylchloroformate (5.4 g; 0.05 mol) and 1,4-diazabicyclo[2.2.2]octane (0.01 g; 0.01 mmol) is added dropwise, methyltricyanosilane (6.05 g; 0.05 mol). The mixture is maintained at between 0° to 30° C. for 2–5 hr. After distilling off the methyltrichlorosilane, the ethyl cyanoformate is isolated by distillation under reduced pressure. The ethylcyanoformate product purity and yield are comparable to those of example 1.

From the above examples and description it will be seen that the advantages of the process can be summarized as follows:

The reaction can be run at room temperature;

The reaction time is short;

Yields are excellent (typically >90%);

The purity of the product is high (exceeding 98%);

The organosilyl chloride, and particularly the trimethylsilyl chloride is readily removed by distillation;

The catalyst can be recycled;

The organosilyl chloride, and particularly trimethylsilyl chloride, can be recycled; and No undesired by-products requiring treatment or disposal are produced.

While the invention has been illustrated by the specific examples set forth above and its fundamental novel features described in detail, it will be understood that various substitutions and changes to the methods and processes disclosed may be made by those skilled in the art without departing from the spirit of the invention. Accordingly, the invention is not to be regarded as limited to the examples disclosed above, but is to be limited only as defined by the claims which follow.

We claim:

1. A process for producing a $C_1$–$C_{20}$ alkyl, aralkyl or aryl cyanoformate ester comprising reacting stoichiometric amounts of a corresponding $C_1$–$C_{20}$ alkyl, aralkyl or aryl haloformate and an organosilyl nitrile selected from the group consisting of dimethyldicyanosilane and methyltricyanosilane, in the presence of a catalytic amount of a tertiary amine base.

2. The process of claim 1 where the tertiary amine base catalyst is selected from the group consisting of triethylamine, 1,4-diazabicyclo[2.2.2]octane,1,8-diazabicyclo[5.4.0]undec-7-ene N,N-dimethylaminopyridine and pyridine.

3. The process of claim 2 where the catalyst is 1,4-diazabicyclo-[2.2.2] octane.

4. The process of claim 1 which is conducted under anhydrous conditions.

5. The process of claim 1 where the haloformate is a chloroformate.

6. The process of claim 1 where the reaction is maintained at a temperature in the range of from about –30° C. to about 70° C.

7. The process of claim 5 where the temperature is in the range from about 5° C. to about 30° C.

8. The process of claim 5 in which the cyanoformate ester product is recovered following removal of chlorosilane.

9. The process of claim 1 which includes the further steps of heating the completed reaction mixture containing the cyanoformate ester product and separately recovering the catalyst and the cyanoformate ester product.

10. The process of claim 9 in which the cyanoformate ester product is recovered by distillation.

11. The process of claim 9 where the recovered catalyst is utilized in producing a subsequent batch of cyanoformate ester product in accordance with the claimed process.

12. A process for producing a cyanoformate ester having the formula $R^1OCOCN$, in accordance with the following reaction scheme:

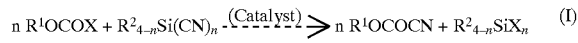

where $R^1$ is selected from the group consisting of alkyl, aralkyl and aryl having from one to twenty carbon atoms, $R^2$ methyl N is 2 on 3, X is a halogen and the catalyst is a tertiary amine base, and the reaction (I) is conducted under anhydrous conditions.

13. The process of claim 12 where $R^1$ is an alkyl containing from one to twenty carbon atoms.

14. The process of claim 12 where X is chlorine.

15. The process of claim 12 where the catalyst is selected from the group consisting of triethylamine, 1,4-diazabicyclo[2.2.2]octane,1,8-diazabicyclo[5.4.0]undec-7-ene and N,N-dimethylaminopyridine.

16. The process of claim 15 here the catalyst is 1,4-diazabicyclo[2.2.2]octane.

17. The process of claim 12 where the organosilyl halide by-product is removed by distillation.

18. The process of claim 12 that is conducted at ambient temperature.

19. The process of claim 12 which includes the further steps of recovering the catalyst and $R^1OCOCN$ by distillation and thereafter recycling the catalyst and organosilyl halide in the further practice of the process.

20. A process for producing a $C_1$–$C_{20}$ alkyl, aralkyl or aryl cyanoformate ester comprising reacting stoichiometric amounts of a corresponding $C_1$–$C_{20}$ alkyl, aralkyl or aryl haloformate and a $C_1$–$C_6$ alkylsilyl nitrile in the presence of a catalytic amount of 1,4-diazabicyclo[2.2.2]octane, recovering the catalyst and the cyanoformate ester product by distillation, and thereafter recycling the catalyst and the $C_1$–$C_6$ alkylsilyl halide reaction by-product in the further practice of the process.

21. The process of claim 20 where the $C_1$–$C_6$ alkylsilyl nitrile is trimethylsilyl nitrile and the alkylhalosilane reaction by-product is trimethylhalosilane.

22. The process of claim 20 where the haloformate is chloroformate and the reaction by-product is trimethylchlorosilane.

* * * * *

UNITED STATES PATENT AND TRADEMARK OFFICE
CERTIFICATE OF CORRECTION

PATENT NO. : 5,852,207
DATED : December 22, 1998
INVENTOR(S) : Jones et al.

It is certified that error appears in the above-identified patent and that said Letters Patent is hereby corrected as shown below:

Column 5,
Line 4, after "diazabicyclo[5.4.0I undec-7-ene" insert a comma.

Column 6,
Line 1, delete "here" and insert -- where --.
Line 7, delete "$^R2$ methyl N is 2 on 3" and insert -- $R_2$ is methyl, n is 2 or 3. --

Signed and Sealed this

Twenty-fifth Day of June, 2002

Attest:

Attesting Officer

JAMES E. ROGAN
*Director of the United States Patent and Trademark Office*